United States Patent [19]
Zajac

[11] Patent Number: 4,857,136
[45] Date of Patent: Aug. 15, 1989

[54] REACTOR MONITORING SYSTEM AND METHOD

[76] Inventor: John Zajac, 1137 Angmar Ct., San Jose, Calif. 95121

[21] Appl. No.: 210,650

[22] Filed: Jun. 23, 1988

[51] Int. Cl.$^4$ ............ H01L 21/306; B44C 1/22; B05D 3/06; C23C 14/00
[52] U.S. Cl. .................... 156/626; 118/712; 118/50.1; 118/620; 156/627; 156/643; 156/646; 156/345; 204/192.13; 204/192.33; 204/298; 427/8; 427/38
[58] Field of Search ............ 156/626, 627, 643, 646, 156/345; 204/192.13, 192.33, 298; 427/8, 38, 39; 118/712-715, 50.1, 620; 356/357, 437

[56] References Cited
U.S. PATENT DOCUMENTS
4,491,499 1/1985 Jerde et al. .................... 156/626
4,611,919 9/1986 Brooks et al. ............... 156/626 X Primary Examiner—William A. Powell
Attorney, Agent, or Firm—Flehr, Hohbach, Test, Albritton & Herbert

[57] ABSTRACT

System and method for detecting problems and other conditions in a semiconducting processing reactor. The relative amounts of two or more substances are monitored, and an output signal is provided when the relative amounts change in a manner corresponding to the change or condition to be detected. In one disclosed embodiment, the substances are ionized to produce excited molecules of the substances, and the substances are sensed with photosensors which are responsive to light of wavelengths characteristic of the substances.

16 Claims, 1 Drawing Sheet

REACTOR MONITORING SYSTEM AND METHOD

This invention pertains generally to the manufacture of semiconductor devices, and more particularly to a system and method for detecting the occurrence of a predetermined condition in the manufacturing process.

Expensive equipment is commonly employed in the manufacture of semiconductor devices in order to obtain the highest possible throughput and yield. Such equipment includes plasma etching and deposition reactors, low pressure chemical vapor deposition reactors, and thin film deposition systems. While such equipment is capable of processing semiconductor devices at a relatively high rate (e.g., thousands of chips per hour), it is difficult to obtain consistent, repeatable results on different machines or even in successive runs on the same machine.

These variation arise because of the difficulty of maintaining identical processing conditions from machine to machine or from run to run on the same machine. Inconsistencies can, for example, arise form errors in the calibration and/or setting of pressure sensors, drift in the operations of flow controllers, power supply variations, and variations in the operation of pumping systems.

Heretofore, it has been necessary to use relatively expensive instruments in order to obtain the consistent operating conditions required for uniform chip processing. Such instruments have included quadrapole mass analyzers, scanning monochrometers and spectral analyzers. In addition to being expensive, such instruments are relatively large and bulky, they are delicate, and they require frequent calibration and maintenance, particularly when subjected to a hostile environment as found in a plasma reactor, for example.

It is in general an object of the invention to provide a new and improved system and method for monitoring conditions in a semiconductor processing reactor.

Another object of the invention is to provide a system and method of the above character which are helpful in eliminating irregularities and inconsistencies in the operation of a reactor.

Another object of the invention is to provide a system and method of the above character which are economical and can be readily employed with existing equipment.

These and other objects are achieved in accordance with the invention by monitoring the conditions in a semiconductor processing reactor to detect the occurrence of a problem or a change of a specific character rather than making a quantitative analysis or determining what the problem is. The relative amounts of two or more substances are monitored, and an output signal is provided when the relative amounts change in a predetermined manner. In one disclosed embodiment, the substances are ionized to produce excited molecules of the substances, and the substances are sensed with photosensors which are responsive to light of wavelengths characteristic of the substances.

Figure 1:
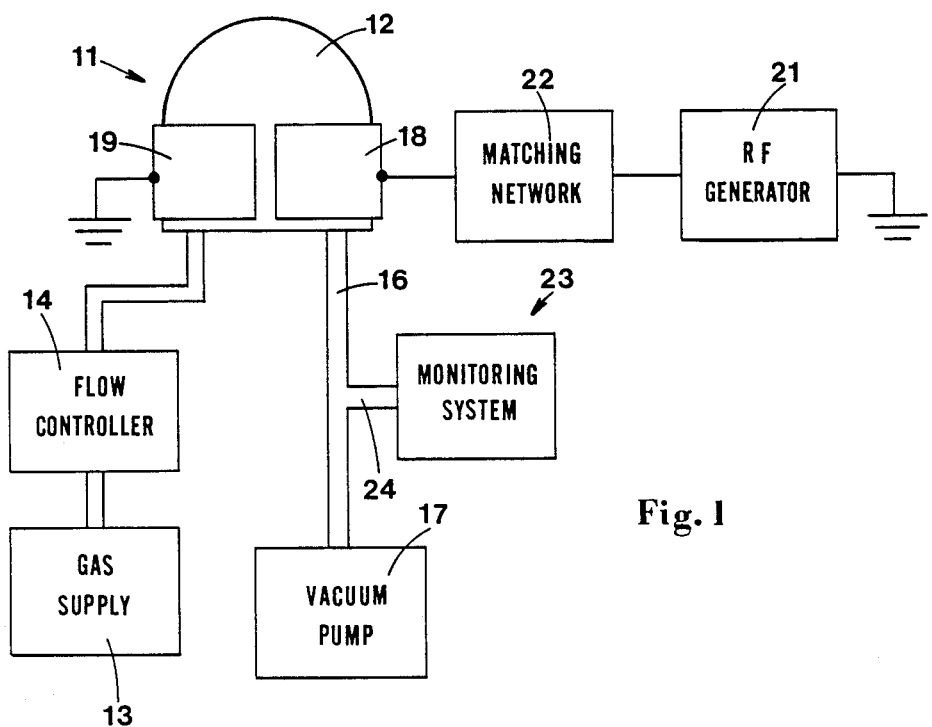
FIG. 1 is a block diagram on one embodiment of a reactor system with a monitor according to the invention.
Figure 2:
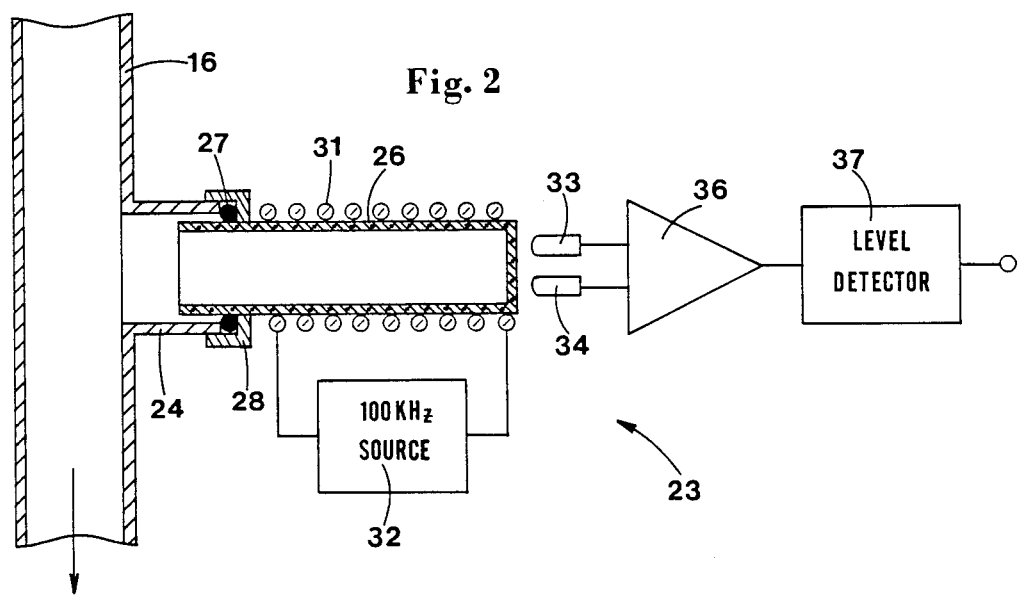
FIG. 2 is a schematic diagram of the monitoring system in the embodiment of FIG. 1.

In the drawings, the invention is illustrated in connection with a plasma reactor system 11. It will be understood, however, that the invention is not limited to plasma reactors and that it can be utilized with other types of reactors including low pressure chemical vapor deposition (LPCVD) reactors and vacuum deposition systems.

Reactor system 11 includes a chamber 12 in which semiconductor wafers (not shown) are processed. Reagent gases are supplied to the chamber from a gas supply 13 and a flow controller 14. Gases are removed from the chamber by an exhaust line 16 and a vacuum pump 17. Gases within the chamber are ionized to form a plasma of excited molecules and active species by an electric field produced by energization of a pair of electrode plates 18, 19 positioned outside the side wall of the chamber. The electrodes are energized by RF energy produced by a generator 21 and coupled to the plates by a matching network 22.

Conditions within the reactor chamber are monitored by a monitoring system 23. In the embodiment illustrated, the monitoring system is connected to the exhaust line 16, and this connection is conveniently made through a leak checking port 24 which is commonly included in such systems. It will be understood, however, that the monitoring system can be connected to the reactor in any suitable manner.

The monitoring system includes a chamber 26 which communicates with exhaust line 16 through port 24 for sampling the gases in the exhaust system. This chamber is fabricated of an electrically nonconductive material, such as quartz, and at least a portion of the chamber is preferably transparent to permit non-invasive monitoring of the conditions within the chamber. An airtight seal is formed between the chamber and the port by a seal ring 27 and a coupling collar 28.

Means is provided for ionizing the gases within chamber 26 to form a low power plasma which emits light characteristic of the gases which are present in the chamber. In the embodiment illustrated, this means includes an induction coil 31 which is positioned coaxially about the chamber and connected to a power source 32. This source can be a relatively low power source such as a 10 watt source operating at a frequency of 100 KHz. Internal electrodes can also be utilized for ionizing the gases within chamber 26, as can other power levels and frequencies, e.g. 60 Hz.

A pair of photodiodes 33, 34 are positioned outside the chamber for sensing the presence of two different gases in the chamber. The photodiodes can be manufactured to be responsive to light of the wavelengths which are characteristic of the gases to be detected, or they can be provided with filters which selectively pass light of the desired wavelengths. The photodiodes produce electrical signals corresponding to the amounts of light of the respective wavelengths impinging thereon.

The output signals from the photodiodes are connected to the inputs of a differential amplifier 36 which provides an output signal corresponding to the ratio of the signals from the photodiodes. The output of the differential amplifier is connected to a level detector 37 which delivers an output signal when the ratio of the photodiode signals reaches a predetermined level corresponding to the condition to be detected in the reactor. This signal can be utilized for shutting down the reactor or adjusting the operating conditions within the reactor, as desired.

Operation and use of the monitoring system, and therein the method of the invention, are as follows. By way of example, it is assumed that the reactor is being employed in a plasma etching process and that the condition to be detected is the end of the etching process. In this example, one of the photodiodes is responsive to the light emitted by excited chlorine molecules, and the other is sensitive to the light emitted by excited water molecules. The ratio of chlorine to water changes throughout the etching process, becoming lower as the process proceeds, and level detector 37 is set to provide an output signal when the ratio drops to the level corresponding to the end of the process.

In addition to detecting the end of a process, the invention can be utilized for detecting a number of conditions such as the starting point, system cleanliness, air leaks, water leaks, pump backstreaming, miscalibrations of a instruments such as capacitance manometers, and malfunctions and miscalibrations of mass flow controllers. In each case, the sensors are selected for monitoring two or more gases or other substances which change in ratio upon occurrence of the condition to be detected, and the level detector is set to respond to this change in ratio. The number of sensors employed in the system can be chosen in accordance with the number of gases or other substances to be monitored.

Typical substances which can be monitored to detect different conditions in a plasma reactor include water, oxygen, pump oil, and gases such as chlorine, fluorine and bromine.

With a plasma reactor, if monitoring is to occur only during the time the plasma is present, it is possible to eliminate chamber 26, inductor 31 and power source 32, and position sensors 33, 34 for monitoring the conditions through the wall of chamber 12.

The invention has a number of important features and advantages. It monitors change in the operation of a reactor to warn of inconsistencies before product quality is affected. It does so simply and inexpensively, which permits the system to be used on virtually all plasma etching and deposition systems as well as vacuum deposition systems and LPCVD systems. It is easy to install and can be readily installed on most existing reactors without affecting the normal operation of the reactors. Utilizing the ratio of the sensor tends to cancel out disturbances which are common to the two sensors, e.g., electrical disturbances contamination of or deposits on the viewing window. Once the existence of a problem has been detected, complete diagnostic analyses can be made with the assistance of more elaborate analytical instruments, and in some instances an experienced operator may be able to identify and correct certain problems without the need for the more expensive equipment.

It is apparent from the foregoing that a new and improved system and method for detecting problems and other conditions in a semiconductor processing reactor have been provided. While only certain presently preferred embodiments have been described in detail, as will be apparent to those familiar with the art, certain changes and modifications can be made without departing from the scope of the invention as defined by the following claims.

I claim:

1. In a system for detecting a change in the operating conditions in a semiconductor processing reactor: sensor means responsive to two different substances for providing signals corresponding to the amounts of the substances which are present, and means responsive to the sensor signals for monitoring the relative amounts of the two substances and providing an output signal when the relative amounts change in a predetermined manner.

2. The system of claim 1 wherein the sensor means comprises first and second photosensors responsive to light of wavelengths characteristic of the two substances.

3. The system of claim 1 wherein the means responsive to the sensor signals includes means for monitoring the ratio of the sensor signals.

4. In a system for detecting the end of a process in a reactor: sensing means for detecting the presence of two different substances, means responsive to the sensing means for monitoring the relative amounts of the two substances, and means responsive to the monitoring means for providing an output signal when the relative amounts of the two substances change in a predetermined manner.

5. The system of claim 4 wherein the sensing means comprises a pair of photosensors responsive to light of different wavelengths characteristic of the two substances.

6. The system of claim 4 including means for ionizing the two substances to produce excited molecules which are detected by the sensing means.

7. In combination: a semiconductor processing reactor, sensor means responsive to two different substances for providing signals corresponding to the amounts of the substances which are present in the reactor, means responsive to the sensor signals for monitoring the relative amounts of the two substances, and means responsive to the relative amounts for providing an output signal.

8. The combination of claim 7 wherein the reactor is a plasma reactor with an exhaust system, and the means sensor means monitors gases in the exhaust system.

9. The combination of claim 8 including means for ionizing the gases in the exhaust system to produce excited molecules of the two substances which are detected by the sensing means.

10. The combination of claim 9 wherein the sensor means comprises first and second photosensors which are responsive to different wavelengths of light emitted by the excited molecules of the two substances.

11. In a method of detecting a change in the operating conditions in a semiconductor processing reactor: monitoring the relative amounts of two substances which are present in the reactor, and providing an output signal when the relative amounts change in a predetermined manner.

12. The method of claim 11 wherein the relative amounts are monitored by sensing light at wavelengths characteristic of the two substances, and taking the ratio of the amounts of light sensed at the respective wavelengths.

13. The method of claim 12 including the step of ionizing the substances to produce excited molecules which emit the light at the characteristic wavelengths.

14. In a method of detecting the end of a process in a reactor: detecting the presence of two different substances in the reactor, monitoring the relative amounts of the two substances, and providing an output signal when the relative amounts of the two substances change in a predetermined manner.

15. The method of claim 14 wherein the presence of the two substances is detected by sensing light at wavelengths characteristic of the two substances.

16. The method of claim 15 including means for ionizing the two substances to produce excited molecules which emit the light at the characteristic wavelengths.

* * * * *